United States Patent [19]

Weissmüller et al.

[11] Patent Number: 5,095,889

[45] Date of Patent: Mar. 17, 1992

[54] ENDOSCOPE FOR LASER LITHOTRIPSY

[75] Inventors: Johannes Weissmüller, Schwaig; Christian Ell; Jürgen Hochberger, both of Erlangen; Ludwig Bonnet, Kntitlingen; Achim Kolb, Bretten, all of Fed. Rep. of Germany

[73] Assignee: Richard Wolf GmbH, Knittlingen, Fed. Rep. of Germany

[21] Appl. No.: 503,190

[22] Filed: Apr. 2, 1990

[30] Foreign Application Priority Data

May 31, 1989 [DE] Fed. Rep. of Germany ....... 3917663

[51] Int. Cl.⁵ .............................................. A61B 17/36
[52] U.S. Cl. ........................................ 128/4; 606/16; 606/127
[58] Field of Search ................... 128/4, 6, 7; 606/13–18, 127–128; 604/20

[56] References Cited

U.S. PATENT DOCUMENTS

| | | | |
|---|---|---|---|
| 2,932,294 | 4/1960 | Fourestier et al. | 128/6 |
| 3,865,113 | 2/1975 | Sharon et al. | |
| 4,211,229 | 7/1980 | Wurster | 606/18 |
| 4,313,431 | 2/1982 | Frank | |
| 4,436,087 | 3/1984 | Ouchi | 128/6 |
| 4,685,449 | 8/1987 | Bonnet | 128/4 |
| 4,693,556 | 9/1987 | McCaughan, Jr. | 606/16 |
| 4,760,840 | 8/1988 | Fournier, Jr. et al. | 606/16 |
| 4,807,595 | 2/1989 | Hiltebrandt | 128/4 |
| 4,819,630 | 4/1989 | DeHart | 606/15 |
| 4,881,524 | 11/1989 | Boebel et al. | 606/16 |

FOREIGN PATENT DOCUMENTS

| | | |
|---|---|---|
| 2945080 | 5/1981 | Fed. Rep. of Germany . |
| 8712715 | 2/1988 | Fed. Rep. of Germany . |
| 3633527 | 4/1988 | Fed. Rep. of Germany . |
| 627936 | 2/1982 | Switzerland . |

Primary Examiner—Stephen C. Pellegrino
Assistant Examiner—Ralph A. Lewis
Attorney, Agent, or Firm—Panitch Schwarze Jacobs & Nadel

[57] ABSTRACT

In an endoscope designed for laser lithotripsy use is made of a laser lithotripsy unit having a guide tube insertable in the barrel of the endoscope, which guide tube encloses a laser light guide which carries at its distal end a fused-on head to concentrate the beam. The laser light guide is guided in the guide tube so as to be axially displaceable and immobilizable, thus making it possible for the distance between the head and the concretion intended for destruction to be adjusted to obtain optimum energy transmission, the relevant conditions being maintained during the operation by virtue of the fact that the distal end of the guide tube for the lithotripsy unit is held in contact with the concretion.

7 Claims, 1 Drawing Sheet

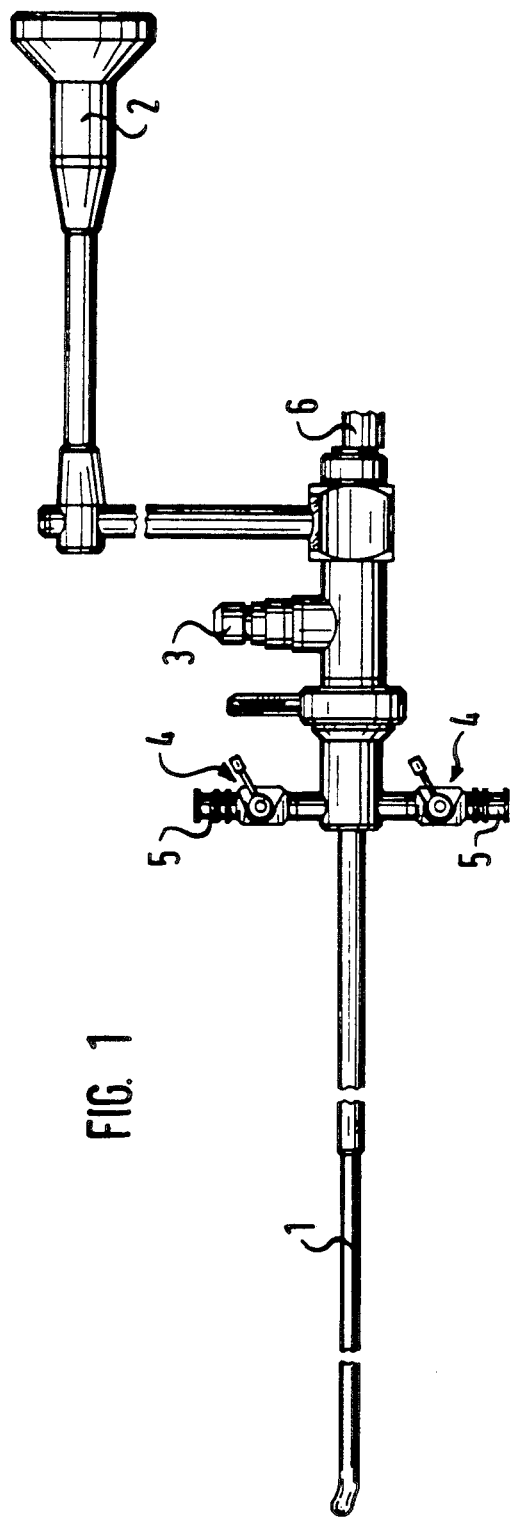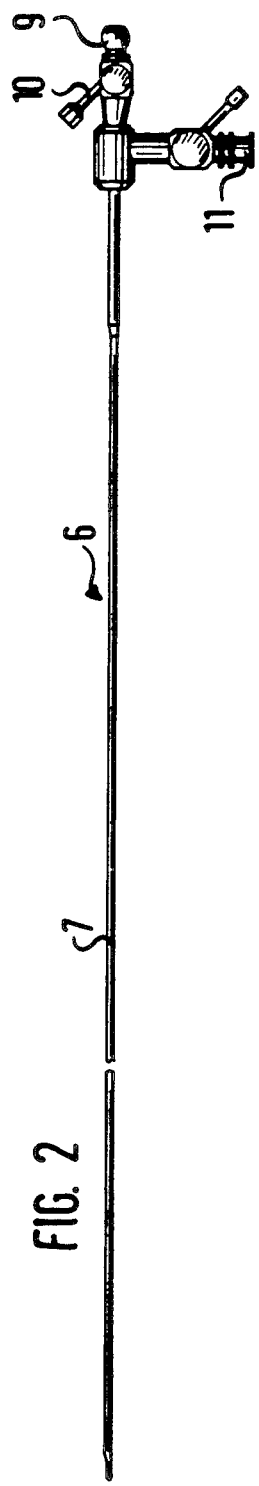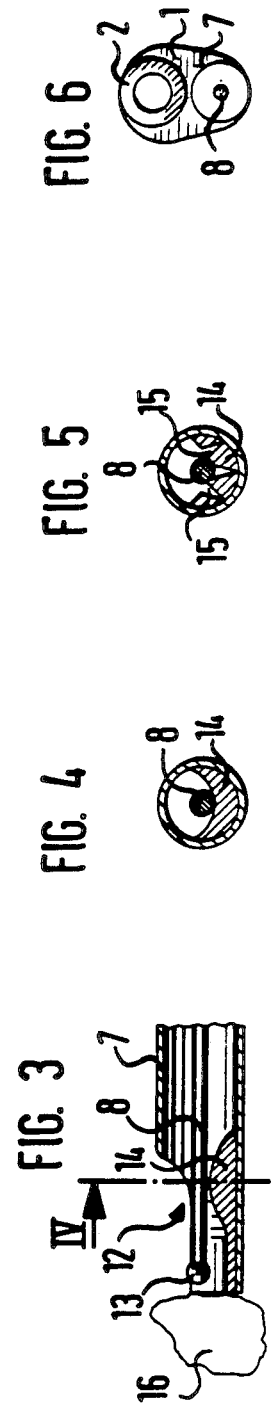

ENDOSCOPE FOR LASER LITHOTRIPSY

BACKGROUND OF THE INVENTION a) Field of the Invention

The invention relates to an endoscope for laser lithotripsy having a light guide connectable proximally to a laser light-source, which guide passes through a passage in the endoscope and can have its distal end lined up under visual control with the concretion to be destroyed by using the telescope of the endoscope.

b) Description of the Prior Art

Endoscopes combinable with laser devices for performing different tasks form a known and commercially available part of medical technology. The prior art includes instruments of this kind which can be employed as surgical scalpels or by means of which bleeding for example can be stopped by coagulation or diseased parts of organs can be selectively bombarded with light. For this purpose the endoscopes generally have insertion passages through which the laser devices can be passed, so that not only is it possible to perform treatments of the kinds which are listed above by way of illustration but also the area of operation can be monitored visually during the treatment process.

As an example, reference may be made to DE-OS 29 45 080 (see U.S. Pat. No. 4,313,431) which relates to an instrument for endoscopic laser irradiation for treating tumours of the bladder. In this instrument, use is made of a tube which encloses a further tube to receive the endoscope plus additional passages which serve to receive or guide, as the case may be, irrigation liquid, a fiber light guide and thrust-rod linkage for aligning the distal end region of the fiber light guide. By means of the thrust-rod linkage the distal end of the light guide can be swivelled off the axis of the instrument and in this way the laser beam can be positioned precisely on the treatment site. Provision is also made for the fiber light guide to be longitudinally displaceable.

Combined with the alignability described above, the purpose of the provisions described is to enable any dirt or fouling on the distal end of the light guide to be removed by moving the distal end forward into the liquid in the bladder and swivelling it from side to side in this position. If the distal end region is dirty, the aim is to avoid having to withdraw it from the patient's body to clean it and then having to re-insert it. Finally, reference will be made to the instrument disclosed in U.S. patent specification No. 3865113 which can be used as a surgical scalpel. In this case too the cutting function is performed by a laser beam, which beam travels through a tubular handpiece and is focussed onto a focussing point by a lens. To allow the instrument to be put into operation, the handpiece is provided with attachments which can be fitted onto it and each of which is adapted to a particular task and forms a guiding element which makes it possible for the surgeon to guide the focussing point in a suitable way for him to perform the operation properly.

In laser lithotripsy, a high-energy laser beam is conveyed to the concretion to be destroyed, this generally being done via a light guide forming part of an endoscopic instrument which is brought up to the concretion in question by being inserted in the relevant body cavity. When this is done, there is a risk of the distal end of the light guide coming into contact with the conretion to be destroyed, which could result in damage to the delicate part in question. It is also important that the transmission of the energy to the concretion should take place repeatably and in an optimum fashion, which makes it necessary for the distance between the distal end of the light guide and the concretion intended for destruction to be accurately adjustable.

The main object of the invention is therefore to design an endoscope of the kind described above in such a way that the requirements mentioned can be met.

SUMMARY OF THE INVENTION

To this end, the present invention consists in an endoscope for laser lithotripsy having a light guide connectable proximally to a laser light-source, which guide passes through a passage in the endoscope and can have its distal end lined up under visual control with the concretion to be destroyed by using the telescope of the endoscope, characterized in that the light guide is arranged in a guide tube which can be inserted into the barrel of the endoscope and can be moved in the axial direction and immobilised in relation thereto in order to allow the distance between the distal end of the guide tube, which can be brought to bear against the concretion, and the end of the light guide tube, to be set and varied.

In a preferred embodiment of the endoscope according to the invention provision is made for the guide tube to have a window open towards the objective of the telescope through which the distal end regions of the guide tube and the light guide can be seen with the telescope. This makes it possible for a visual check to be kept on what is being done in the region of the working area of the instrument.

In a further embodiment of the invention at least the distal end region of the light guide is supported in the guide tube and is guided axially, and in particular coaxially, therein, in which case the support which guides the light guide may be provided on the side of the guide tube opposite from the window and the support may be in the form of a ramp having a guiding face parallel to the axis of the guide tube.

The light guide may be immobilised axially in the optimised position by actuating proximal clamping means through which the light guide was inserted into the guide tube.

In another embodiment, the distal end of the light guide may be formed by a head fused to the fiber. The head, which is preferably spherical in shape, concentrates the beam, thus generating a plasma in front of the end face of the light guide which produces a shock wave against the concretion.

Finally, an embodiment of the endoscope has proved particularly advantageous in which the open lumen between the light guide and the guide tube forms a distally open passage for irrigation water, which water can be fed into the passage via a proximal connection and, having emerged form the passage, can be withdrawn from the treatment site via a further passage which is formed by the open lumen between the guide tube and telescope on the one hand and the barrel of the endoscope on the other and which opens into a proximal connection on the barrel of the endoscope. The particular advantage of this arrangement lies in the fact that the irrigation jet is directed straight onto the point of destruction and hence the particles forcibly dislodged are at once removed from the area of which the laser beam acts, thus improving the effectiveness of the latter still further.

BRIEF DESCRIPTION OF THE DRAWINGS

In order that the invention may be more readily understood some embodiments thereof will now be described, by way of example, with reference to the accompanying drawings, in which:

FIG. 1 is a general view of an endoscope designed for lithotripsy,

FIG. 2 shows a laser lithotripsy unit which is made according to the invention and which has a laser light guide and is insertable in the barrel of the endoscope, FIG. 3 is enlarged longitudinal section through the distal end region of the unit shown in FIG. 2, FIG. 4 is a cross-section taken along the line IV through the distal end region of the unit which is shown in FIG. 3, FIG. 5 is a cross-section as in FIG. 4 through another embodment of the distal end region shown in FIG. 3, and FIG. 6 is a cross-section through the barrel of the endoscope with the laser lithotripsy unit inserted.

DESCRIPTION OF THE PREFERRED EMBODIMENTS

In FIG. 1 there is shown an endoscope which is employed in practice in the conventional manner. In essence, it comrprises a barrel 1 in whose proximal end region are arranged an endoscopic telescope 2 for monitoring the working area visually, a light connection 3 for illuminating the working area, adjusting means 4 for controlling the angular deviation of the distal end of the endoscope barrel 1 from the axis of the remainder of the barrel, and connections 5 for feeding in and draining out irrigating liquid. The barrel 1 of the endoscope serves to receive and to have passed through it a laser lithotripsy unit 6 as shown in FIG. 2. This unit 6 comprises, in essence, a guide tube 7 which is used to hold a light guide 8 in a co-axial position. In the region of its proximal end the guide tube 7 has a light guide connector 9 connected to the light guide 8 and clamping means 10 for immobilising the light guide 8 axially. Also provided in the said end region is connection 11 for an irrigant medium.

Running back from the exit window for the telescope at the distal end of the endoscope, part of the tubular shell of the guide tube 7 is removed to provide the distal end region of the guide tube 7 with a window 12 as can be seen from FIG. 3, thus allowing said end region to be adjusted with aid of the telescope 2 relative to the concretion intended for destruction. When the distal end of the light guide 8 is advanced into this region, it too can be monitored visually in this way, the said end being formed by a head 13 which is fused to the light guide. To guide the distal end region of the light guide 8 in a central position and to maintain it there, a support 14 which supports the light guide 8 in a vee guide is mounted in position on the side of the guide tube 7 opposite from the window. So that the irrigating liquid can also pass through on the side where the support 14 is situated, the support may be provided with longitudinal grooves 15 as shown in FIG. 5.

In the instrument according to the invention the stream of liquid is directed straight onto the point being operated on and this makes it possible for the forcibly dislodged particles of a concretion 16 to be washed at once out of the field of action of the laser beam. The irrigating liquid then flows back through the relatively wide lumen between the barrel 1 of the endoscope and the guide tube 7 of the lithotripsy unit 6, thus enabling the laser beam to be used with great effectiveness. The irrigating liquid flows in through the connection 11 for irrigating medium, thus enabling both the connections 5 to be used as outflow connections.

Whilst particular embodiments have been described, it should be appreciated that the invention includes all modications and variations falling within its scope.

We claim:

1. An endoscope for laser lithotripsy comprising a barrel, a telescope located in the barrel and a light guide which is connectable proximally to a laser light source, said light guide passing through a guide tube which is insertable into said barrel of the endoscope and whose distal end under visual control by the telescope is alignable with a concretion to be destroyed, said light guide being axially movable in said guide tube, means for immobilizing said light guide so that its distal end is spaced from the distal end of the guide tube, characterized by said guide tube having two sides wherein a window on one side is open toward the objective of said telescope, through which the distal end regions of the guide tube and the light guide can be seen through the telescope, and at least the distal end region of the light guide being axially guided and supported in the guide tube by a support which is located in the guide tube on the side opposite to the window.

2. An endoscope according to claim 1, wherein the guide tube has an axis and the support is in the form of a ramp having a guiding face parallel to the axis of the guide tube.

3. An endoscope according to claim 1, wherein the light guide is insertable in the guide tube via a proximal clamping means and can be immobilized by actuating the clamping means.

4. An endoscope according to claim 1, wherein the distal end of the light guide is formed by a laser beam concentrating head fused thereto.

5. A endoscope according to claim 1, wherein the light guide and the guide tube define a first open lumen therebetween which forms a distally open passage for irrigation water, which water can be fed into the passage via a proximal connection and, having emerged from the passage, can be withdrawn from the site of concretion destruction via a further passage which is defined by a second open lumen between the guide tube and telescope on the one hand and the barrel of the endoscope on the other hand and which opens into a proximal connection on the barrel of the endoscope.

6. An endoscope according to claim 1 wherein said support guides and supports said light guide co-axially in said guide tube.

7. An endoscope according to claim 1 wherein said support has grooves extending longitudinally of said guide tube to allow passage of irrigating liquid.

* * * * *